(12) United States Patent
Ochs et al.

(10) Patent No.: US 7,785,457 B2
(45) Date of Patent: Aug. 31, 2010

(54) SENSOR ELEMENT AND METHOD FOR DETERMINING AMMONIA

(75) Inventors: Thorsten Ochs, Schwieberdingen (DE); Helge Schichlein, Karlsruhe (DE); Sabine Thiemann-Handler, Stuttgart (DE); Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 1183 days.

(21) Appl. No.: 10/933,095

(22) Filed: Sep. 2, 2004

(65) Prior Publication Data
US 2005/0098449 A1 May 12, 2005

(30) Foreign Application Priority Data
Sep. 3, 2003 (EP) ................................. 03019972

(51) Int. Cl.
*G01N 27/27* (2006.01)
(52) U.S. Cl. ................... 204/424; 204/425; 204/426; 205/783.5; 73/23.31; 73/23.32
(58) Field of Classification Search ......... 204/421–432; 205/781–786; 73/23.31–23.32
See application file for complete search history.

(56) References Cited

U.S. PATENT DOCUMENTS

| 4,432,939 | A | * | 2/1984 | Watanabe et al. | ............. 422/93 |
|---|---|---|---|---|---|
| 4,985,126 | A | | 1/1991 | Haefele et al. | |
| 6,455,009 | B1 | * | 9/2002 | Kato et al. | .................. 422/110 |
| 6,495,027 | B1 | * | 12/2002 | Stahl et al. | .................. 205/781 |
| 2003/0089101 | A1 | * | 5/2003 | Tanaka et al. | .................. 60/285 |
| 2003/0121801 | A1 | * | 7/2003 | Inaba et al. | ............... 205/785.5 |

FOREIGN PATENT DOCUMENTS

| DE | 198 51 949 | 10/2000 |
|---|---|---|
| DE | 199 30 636 | 1/2001 |
| DE | 101 21 771 | 11/2002 |
| EP | 10 01 262 | 5/2000 |
| JP | 2000-193639 | 7/2000 |
| WO | 00/57169 | 9/2000 |

* cited by examiner

*Primary Examiner*—Nam X Nguyen
*Assistant Examiner*—Bach T Dinh
(74) *Attorney, Agent, or Firm*—Kenyon & Kenyon LLP

(57) ABSTRACT

A sensor element of a gas sensor, which is used for determining the concentration of ammonia and, optionally, at least one further component of a gas mixture, in particular in exhaust gases of combustion engines. The sensor element includes at least one first auxiliary electrode and at least one measuring electrode positioned downstream in the flow direction of the gas mixture, which are in direct contact with the gas mixture, a signal generated by the measuring electrode being used at least intermittently for determining the concentration of ammonia. A potential, at which ammonia contained in the gas mixture is oxidized, is applied at least intermittently to the first auxiliary electrode or the measuring electrode.

12 Claims, 2 Drawing Sheets

SENSOR ELEMENT AND METHOD FOR DETERMINING AMMONIA

FIELD OF THE INVENTION

The present invention relates to a sensor element of a gas sensor and a method for determining the concentration of ammonia and, optionally, a further component of a gas mixture.

BACKGROUND INFORMATION

In the course of increasingly stringent environmental guidelines, the sensory system in the region of combustion-engine exhaust gases is becoming increasingly important. In this context, particularly gas sensors based on solid electrolyte are used, which identify the gaseous components to be detected in the exhaust gas in a highly selective manner. In combustion engines operated with a hyperstoichiometric amount of air, the formation of nitrogen oxides is increased. In order to be able to remove them from the exhaust gas, emission-control systems based on the addition of reductive substances to the exhaust system are important. For example, ammonia or ammonia-releasing substances such as urea are used for this purpose. Since besides the emission of nitrogen oxides, the release of ammonia into the environment should also be prevented, the demand for gas sensors, which are suitable for determining both ammonia and reducible gases such as nitrogen oxides, is increasing.

German patent document no. 199 30 636 discusses and refers to a solid-electrolyte-based gas sensor, which is used to detect nitrogen oxides. The measuring principle of the sensor is based on the fact that, inside the gas sensor, excess oxygen is removed without affecting the nitrogen-oxide concentration, a constant, low oxygen concentration being set at a first pump electrode. Then, first of all, the concentration of remaining oxygen and, secondly, the sum of the concentrations of remaining oxygen and nitrogen oxides are concurrently determined in an amperometric manner. The nitrogen-oxide concentration is simple to calculate by forming the difference of the two signals. However, this sensor is limited to determining the concentration of oxygen and nitrogen oxides.

SUMMARY OF THE INVENTION

In contrast, the exemplary embodiment and/or exemplary method of the present invention is based on the object of providing a sensor element for a gas sensor and a method, which reliably ensure the determination of ammonia and, optionally, a further component in a gas mixture and may still be inexpensively manufactured.

The sensor element of the present invention and the exemplary method of the present invention, as described herein, possess the advantage that they may reliably allow the ammonia concentration of a gas mixture to be determined. To this end, a potential, at which the ammonia present in the gas mixture is oxidized, is advantageously applied to a measuring electrode or an auxiliary electrode of the sensor element. In the process, nitrogen monoxide and, to a secondary extent, nitrogen dioxide, dinitrogen monoxide, and, in some instances, further nitrogen oxides are formed as oxidation products. If a potential, at which ammonia is oxidized, is applied to a measuring electrode, then the ammonia concentration of the gas mixture may be determined in a simple manner by simply determining the pump current flowing between the measuring electrode and a counterelectrode.

If a potential, at which ammonia is oxidized, is applied to an auxiliary electrode, then nitrogen oxides, in particular nitrogen monoxide, are formed, the measuring techniques of whose determination are relatively simple to implement. Thus, e.g. a potential, at which the nitrogen oxides formed during the oxidation of ammonia are reduced, may be applied to a measuring electrode positioned in the interior of the sensor element, downstream in the flow direction of the gas mixture. The pump current flowing between a counterelectrode and the measuring electrode in this instance may be detected in a simple manner and used to determine the concentration of ammonia originally present in the gas mixture.

Advantageous further refinements and improvements of the sensor element and method are described herein. Thus, it is, for example, believed to be advantageous when the sensor element has two measuring electrodes in its interior; the two measuring electrodes each being preceded by an auxiliary electrode, at which the ammonia contained in the gas mixture is oxidized. A further auxiliary electrode, at which nitrogen oxides already contained in the gas mixture from the start are decomposed, is placed in front of at least one of the two auxiliary electrodes. Such a sensor element advantageously allows the sum of the nitrogen-oxide amount resulting from the oxidation of ammonia and the nitrogen oxide amount already present in the gas mixture from the start to be determined, using the first measuring electrode, and the concentration of nitrogen oxides formed exclusively during the oxidation of the ammonia contained in the gas mixture to be determined, using the second measuring electrode. The calculation of the difference of the two measuring signals allows the concentration of ammonia and the concentration of the nitrogen oxides already contained in the gas mixture from the start to be determined in an exact manner, independently of each other.

In a particularly advantageous, specific embodiment, only one measuring electrode and two auxiliary electrodes placed in front of the measuring electrode are provided. In a first time interval, nitrogen oxides present in the gas mixture and oxygen contained therein are removed at the first auxiliary electrode, and ammonia present in the gas mixture is oxidized at the second auxiliary electrode. The nitrogen oxides formed in the process are reduced at the measuring electrode. The nitrogen-oxide concentration that is measurable in this instance corresponds to the concentration of ammonia present in the gas mixture.

In a second time interval, only oxygen is reduced and ammonia oxidized at at least one auxiliary electrode, so that ammonia-oxidation products contained in the gas mixture may reach the measuring electrode in the form of nitrogen oxides. In this manner, the sum of the nitrogen oxides already present in the gas mixture and the nitrogen oxides forming during the oxidation of ammonia is determined at the measuring electrode, in the second time interval. The concentration of ammonia and the concentration of nitrogen oxides contained in the gas mixture from the start may be determined, from the calculation of the difference of the measuring signal in the second time interval minus the measuring signal in the first time interval. This allows a particularly simple sensor layout, while simultaneously having high measuring accuracy.

DETAILED DESCRIPTION

Figure 1:
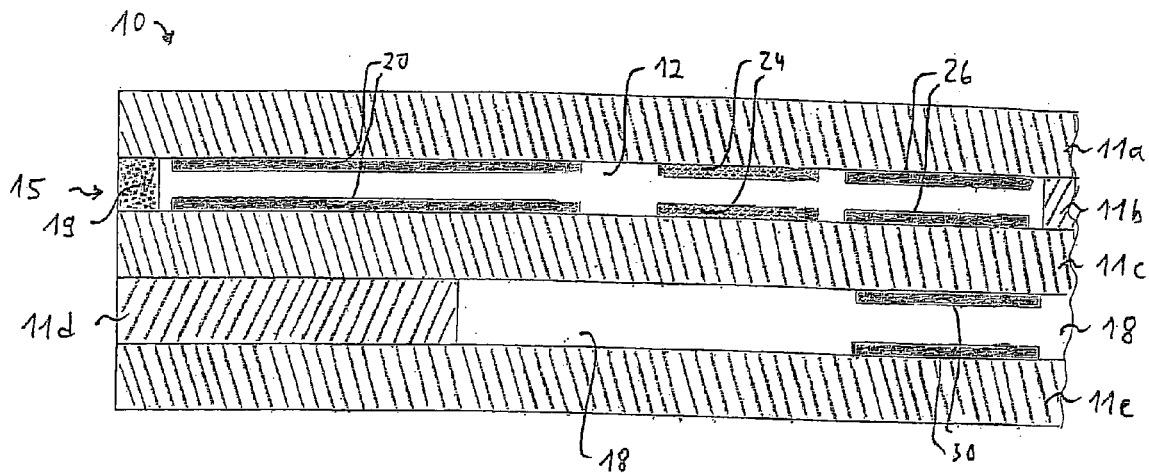
FIG. 1 shows a longitudinal cross section of a measuring-gas-side portion of a sensor element according to the present invention, in the vertical direction, according to a first exemplary embodiment.

FIG. 1 shows a schematic of the structure of a first specific embodiment according to the present invention. Reference numeral 10 designates a planar sensor element of an electrochemical gas sensor, which is used for determining ammonia and, optionally, a further component of a gas mixture, which may be in exhaust gases of combustion engines. The sensor element has a plurality of oxygen-ion-conducting, solid-electrolyte layers 11a, 11b, 11c, 11d, and 11e, which are designed, for example, as ceramic foils and form a planar ceramic body. They are made of a solid-electrolyte material that conducts oxygen ions, such as $ZrO_2$ stabilized or partially stabilized with $Y_2O_3$.

The integrated form of the planar ceramic body of sensor element 10 is produced in a manner known per se, by laminating together the ceramic foils printed over with functional layers and subsequently sintering the laminated structure.

Sensor element 10 contains, for example, an inner gas compartment 12 and a reference-gas channel 18. Via a gas intake, which leads out of the planar body of sensor element 10 at one end, reference-gas channel 18 is in contact with a reference gas atmosphere, which is formed by surrounding air, for example.

Inner gas compartment 12 has an opening 15, which allows for contact with the gas mixture to be analyzed. Opening 15 is provided in solid electrolyte layer 11b, but it may also be placed in solid-electrolyte layer 11a, in a direction perpendicular to the upper surface of sensor element 10.

A resistance heater is also embedded in the ceramic base of sensor element 10, between two electrical insulation layers not shown. The resistance heater is used to heat sensor element 10 up to the required operating temperature of, e.g. 600 to 900° C.

A first auxiliary electrode 20 is formed in inner gas compartment 12, which may be in duplicate. A second auxiliary electrode 24 is positioned downstream in the diffusion direction of the gas mixture, which may be in duplicate, as well. A reference electrode 30 is situated in reference-gas channel 18.

Together with reference electrode 30 as a counterelectrode, auxiliary electrodes 20, 24 each form electrochemical pump cells. A constant partial pressure of oxygen, which is less than that of the gas mixture, is set in the inner gas compartment 12 by first pump cell 20, 30.

Inside inner gas compartment 12, a porous. diffusion barrier 19 is situated in front of first auxiliary electrodes 20 in the diffusion direction of the gas mixture. Porous diffusion barrier 19 constitutes a diffusion resistor with regard to the gas mixture diffusing towards first auxiliary electrodes 20.

If the diffusion resistance of diffusion barrier 19 is selected to be sufficiently large, then electrochemical pump cells 20, 30; 24, 30 may be operated in the so-called limit-current range, in which, in each instance, the gases to be decomposed are completely converted at the corresponding electrode surfaces and the resulting pump current is consequently limited. However, such an operating method is not essential.

In inner gas compartment 12, a further porous diffusion barrier may additionally be provided between first auxiliary electrodes 20 and second auxiliary electrodes 24, in order to stabilize the setting-in (formation) of different oxygen concentrations in different regions of inner gas compartment 12.

Additionally situated in inner gas compartment 12, downstream from auxiliary electrodes 20, 24 in the diffusion direction of the gas mixture, is a measuring electrode 26, which, together with reference electrode 30, which may form a further pump cell and is made of a catalytically active material, such as rhodium, a platinum-rhodium alloy, or another suitable platinum alloy. Reference electrode 30 is also made of a catalytically active material, such as platinum. In this context, the electrode material for all electrodes is applied (used) in an available manner and is referred to as cermet, in order to sinter the electrode material to the ceramic foils.

According to a first specific embodiment of the present invention, the concentration of the ammonia present in the gas mixture is determined in a first time interval with the aid of pump cell 26, 30, and, in a second time interval, the sum of the concentrations of ammonia present in the gas mixture and nitrogen oxides present in the gas mixture from the start are determined. Thus, the measuring signal acquired in the first time interval yields a direct measure of the concentration of ammonia present in the gas mixture. In addition, the concentration of nitrogen monoxide present in the gas mixture is obtained by simply forming the difference of the measuring signals acquired in the first and second time intervals, or, in the case of a suitable potential at measuring electrodes 26, the concentration of all nitrogen oxides present in the gas mixture is obtained.

To this end, a potential, at which the oxygen present in the gas mixture and the nitrogen oxides present in the gas mixture are reduced and, as a result, at least largely removed from the gas mixture, is applied to first auxiliary electrodes 20 in the first time interval. However, the potential applied to first auxiliary electrodes 20 is selected so that ammonia present in the gas mixture is not decomposed. The selected potential is, e.g. −400 to −900 mV with respect to the potential of air-reference electrode 30. The selectivity of first auxiliary electrodes 20 may be further increased by selecting a suitable electrode material for them. To this end, auxiliary electrodes 20 are made, for example, of basic oxides such as $K_2O$, $Li_2O$ or oxides of rare-earth metals. Even precious-metal electrodes impregnated with basic oxides are suitable.

In the first time interval, a potential, which results in a further decrease of the concentration of oxygen still contained in the gas mixture and a quantitative oxidation of the ammonia contained in the gas mixture to nitrogen oxides, in particular nitrogen monoxide, is additionally applied to second auxiliary electrodes 24. In addition, e.g. the hydrogen contained in the gas mixture is oxidized. To this end, a potential of −200 to −700 mV with respect to air-reference electrode 30 is applied to second auxiliary electrodes 24. Second auxiliary electrodes 24 are made of a suitable material, for example platinum or a platinum alloy.

In the first time interval, a potential of −200 to −500 mV, at which the nitrogen oxides contained in the gas mixture, in particular nitrogen monoxide, are quantitatively reduced and the pump current flowing to measuring electrodes 26 in the process is detected, is applied to measuring electrodes 26. The pump current is a direct measure of the concentration of ammonia originally present in the gas mixture.

An alternative operating method in the first time interval is to apply a potential to first and/or second auxiliary electrode 20, 24, at which only oxygen and/or nitrogen oxides are reduced and removed from the gas mixture, and to provide a potential at measuring electrodes 26, at which ammonia present in the gas mixture is oxidized. In this instance, the pump current flowing from measuring electrode 26 to reference electrode 30 is used as a measure of the concentration of ammonia in the gas mixture.

In the second time interval, a potential, at which the oxygen concentration of the gas mixture is selectively reduced without the nitrogen oxides present in the gas mixture being decomposed, is applied to first auxiliary electrodes 20. At the same time, the ammonia present in the gas mixture is oxidized. The potential is selected to be, for example, −200 to −400 mV with respect to air-reference electrode 30.

In the second time interval, as in the first time interval, ammonia still present in the gas mixture is oxidized at second auxiliary electrodes 24 to form corresponding nitrogen oxides, in particular nitrogen monoxide. At the same time, the concentration of oxygen still present in the gas mixture is further reduced, and hydrogen contained in the gas mixture is oxidized. In this manner, measuring electrode 26 displays a low cross sensitivity to the hydrogen concentration of the gas mixture to be measured. In this context, a potential of −200 to −400 mV is provided at second auxiliary electrodes 24.

In the second time interval, nitrogen oxides, in particular nitrogen monoxide, are reduced at measuring electrodes 26, the nitrogen oxides resulting, first of all, from the oxidation of ammonia, and possibly having been, second of all, components of the gas mixture from the start. Consequently, in the second time interval, the sum of the concentrations of nitrogen oxides resulting from the oxidation of ammonia and nitrogen oxides already present in the gas mixture from the start is determined by pump cell 26, 30. To this end, as in the first time interval, a potential of −200 to −500 mV with respect to air-reference electrode 30 is applied to measuring electrodes 26.

An alternative operating method of sensor element 10 is to dispense with an oscillating operation having a first and a second time interval and instead maintain the operating method described for the first time interval for the entire operating time. This simplifies the metrological control of the sensor element. However, this operating method does not allow both the ammonia concentrations and the concentration of nitrogen oxides present in the gas mixture to be measured.

Figure 2:
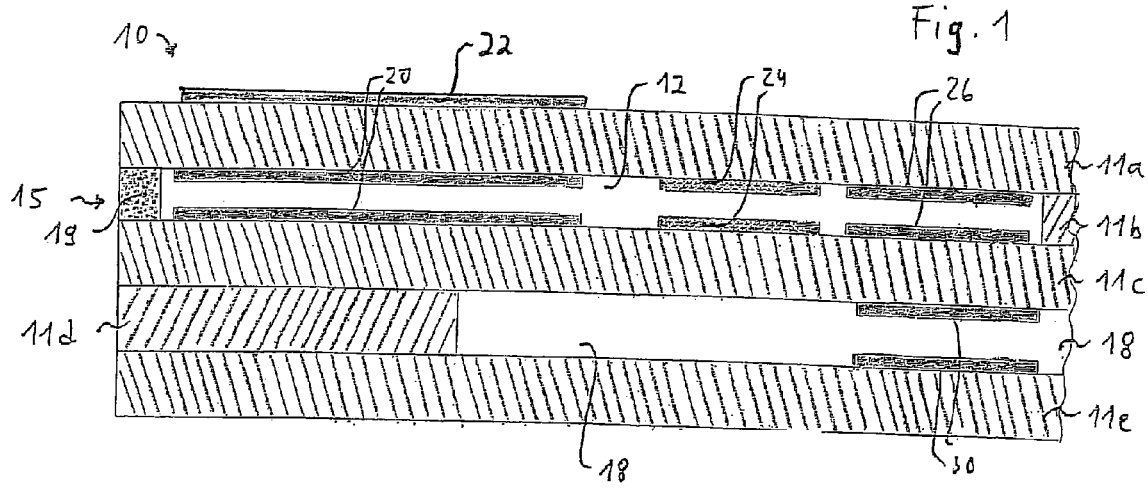
FIG. 2 shows a longitudinal cross section of the measuring-gas-side portion of a sensor element according to the present invention, in the vertical direction, according to a first variant of the first exemplary embodiment.

FIG. 2 shows a variant of the present sensor element according to the first exemplary embodiment. In this context, identical reference numerals designate the same components as in FIG. 1. On an outer surface, the sensor element represented in FIG. 2 has an outer pump electrode 22, which, as a counterelectrode, forms, in each instance, electrochemical pump cells together with auxiliary electrodes 20, 24. In this case, in order to monitor the set partial pressure of oxygen, at least one of auxiliary electrodes 20, 24 and reference electrode 30 are additionally connected together to form a so-called Nernst or concentration cell. This allows the oxygen potential of auxiliary electrodes 20, 24, which is a function of the oxygen concentration in inner gas compartment 12, to be directly compared to the constant oxygen potential of reference electrode 30 in the form of a measurable electrical voltage. The level of the pump voltage to be applied to first pump cell 20, 22 is selected so that the electrical voltage measured at concentration cell 24, 30 assumes a constant value.

Alternatively, or in addition, measuring electrode 26 may form, together with outer pump electrode 22, additional pump cell 22, 26, and measuring electrode 26 may form, together with reference electrode 30, a further concentration cell 26, 30. This permits an alternative or additional option for monitoring the partial pressure of oxygen present in inner gas compartment 12.

Figure 3:
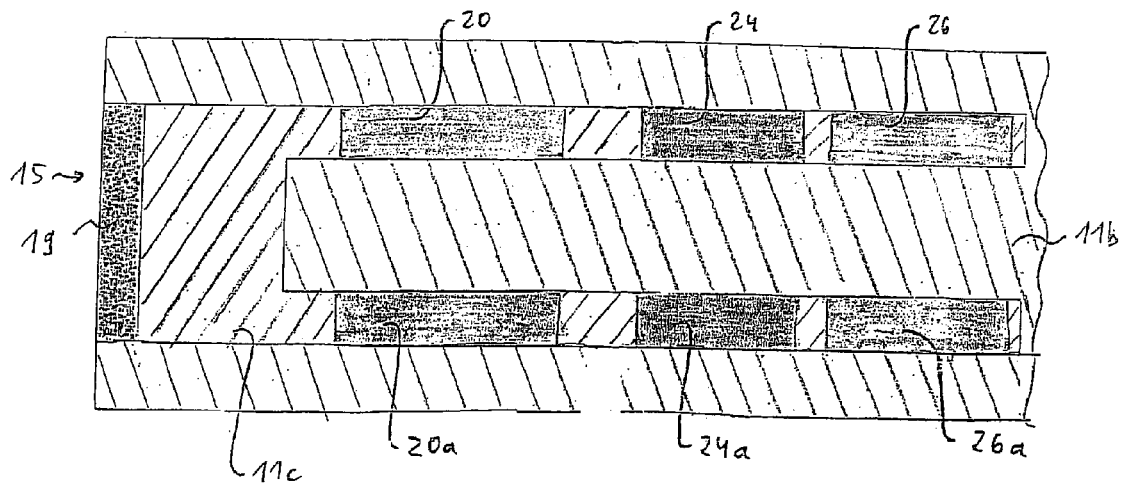
FIG. 3 shows a longitudinal cross-section of the measuring-gas-side portion of a sensor element on the side of the measuring gas, in the horizontal direction, at the elevation of solid-electrolyte layer 11b, according to a second exemplary embodiment.

A second exemplary embodiment of the present sensor element is represented in FIG. 3. In this context, identical reference numerals designate the same components as in FIG. 1 or 2. FIG. 3 shows a horizontal longitudinal cross-section of the measuring-gas-side portion of a sensor element 10, at the elevation of solid-electrolyte layer 11*b*, according to a second exemplary embodiment. This sensor element has two measuring-gas compartments 12, 12*a*, which are in contact with each other in the region of opening 15 and are separated from the gas mixture surrounding the sensor element by a common diffusion barrier 19. In this context, measuring-gas compartment 12 has a first auxiliary electrode 20, a second auxiliary electrode 24, and a measuring electrode 26, and second measuring-gas compartment 12*a* has a further, first auxiliary electrode 20*a*, a further, second auxiliary electrode 24*a*, and a further measuring electrode 26*a*.

During operation of the sensor element, the potentials provided during the first time interval in the case of the sensor element according to the first exemplary embodiment are provided at electrodes 20, 24, 26 of measuring-gas compartment 12. This means that a potential of −400 to −900 mV, at which nitrogen oxides contained in the gas mixture are removed and the concentration of oxygen contained in the gas mixture is reduced, is applied to first auxiliary electrodes 20. A potential of −200 to −700 mV, at which the oxygen concentration of the gas mixture is further reduced and ammonia contained in the gas mixture and/or the hydrogen contained in the ammonia is oxidized, is applied to second auxiliary electrodes 24. When a potential of −200 to −500 mV is applied to measuring electrodes 26, the nitrogen monoxide formed during the oxidation of ammonia is reduced and the pump current flowing between measuring electrode 26 and reference electrode 30 in this instance is determined and used as a measure of the ammonia concentration of the gas mixture.

An alternative operating method is to apply a potential to first and/or second auxiliary electrode 20, 24, at which only oxygen and/or nitrogen oxides are reduced and removed from the gas mixture, and to provide a potential at measuring electrode 26, at which ammonia present in the gas mixture is oxidized. In this context, the pump current flowing from measuring electrode 26 to reference electrode 30 is used as a measure of the concentration of ammonia in the gas mixture.

At the same time, a potential may be applied to electrodes 20*a*, 24*a*, 26*a* of second measuring-gas compartment 12*a*, as is already described within the scope of the first exemplary embodiment, inside the second time interval, for electrodes 20, 24, 26.

Thus, a potential of −200 to −400 mV, at which the oxygen concentration of the gas mixture is indeed reduced and ammonia present in the gas mixture is oxidized, but the concentration of nitrogen oxides is not changed, is applied to further, first auxiliary electrodes 20*a*. When a potential of −200 to −400 mV is applied to further, second auxiliary electrodes 24*a*, ammonia still remaining is oxidized to nitrogen monoxide. Applied to further measuring electrodes 26*a* is a potential of −200 to −500 mV, at which both the portion of nitrogen monoxide formed during the oxidation of ammonia at further auxiliary electrodes 20*a*, 24*a* and the portion of nitrogen monoxide already contained in the gas mixture from the start are reduced. The pump current flowing between reference electrode 30 and further measuring electrodes 26a in this instance is a measure of the sum of the concentration of the ammonia contained in the gas mixture plus the concentration of nitrogen monoxide already present in the gas mixture from the start.

The sensor element according to the second exemplary embodiment allows both the concentration of ammonia in the gas mixture and the sum of the ammonia and nitrogen-monoxide concentrations to be synchronously determined. The concentration of nitrogen monoxide is obtained from the difference of the two measuring signals. In this case, an oscillating operation, as described within the scope of the first exemplary embodiment, may be omitted.

Figure 4:
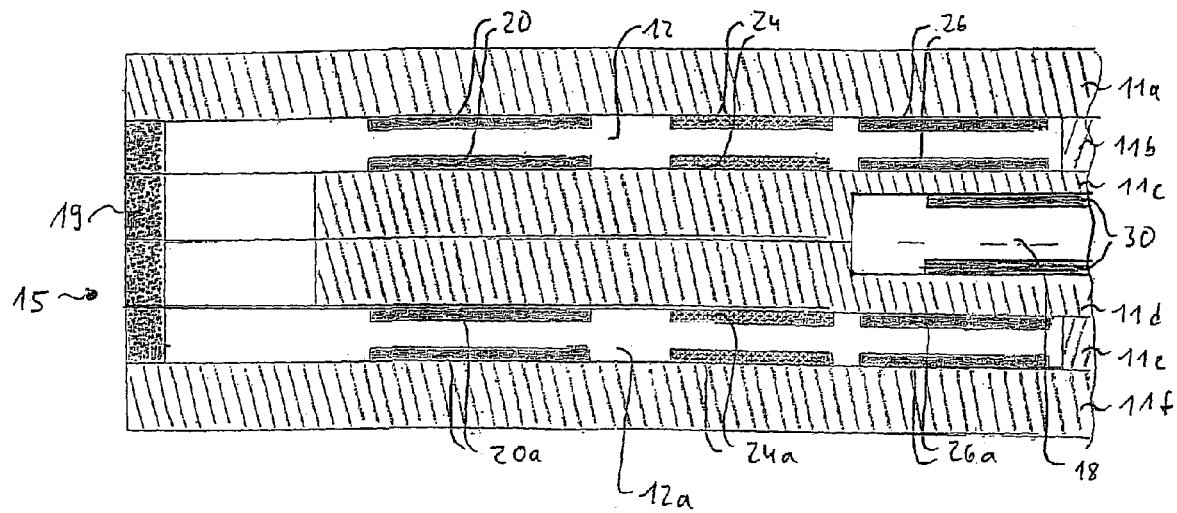
FIG. 4 shows a longitudinal cross section of the measuring-gas-side portion of a sensor element according to a third exemplary embodiment, in the vertical direction, according to a third exemplary embodiment.

A further exemplary embodiment of the present invention is shown in FIG. 4. In this context, identical reference numerals continue to designate the same components. As in the case of the sensor element according to the second exemplary embodiment, the sensor element according to the third exemplary embodiment has two measuring-gas compartments 12, 12a. In contrast to the sensor element represented in FIG. 3, measuring-gas compartments 12, 12a are situated in different layer planes 11b, 11e, one below the other. In addition, the sensor element according to the third exemplary embodiment has, for example, a further solid-electrolyte layer 11f. Measuring-gas compartments 12, 12a may be positioned symmetrically with respect to reference-gas channel 18. The operating method of electrodes 20, 20a, 24, 24a, 26, 26a corresponds to the one previously described within the scope of the second exemplary embodiment. A common diffusion barrier 19 is connected in series to and in front of the two measuring-gas compartments 12, 12a. In this manner, the gas mixture diffusing into measuring-gas compartments 12, 12a is subject to the same diffusion resistance.

Figure 5:
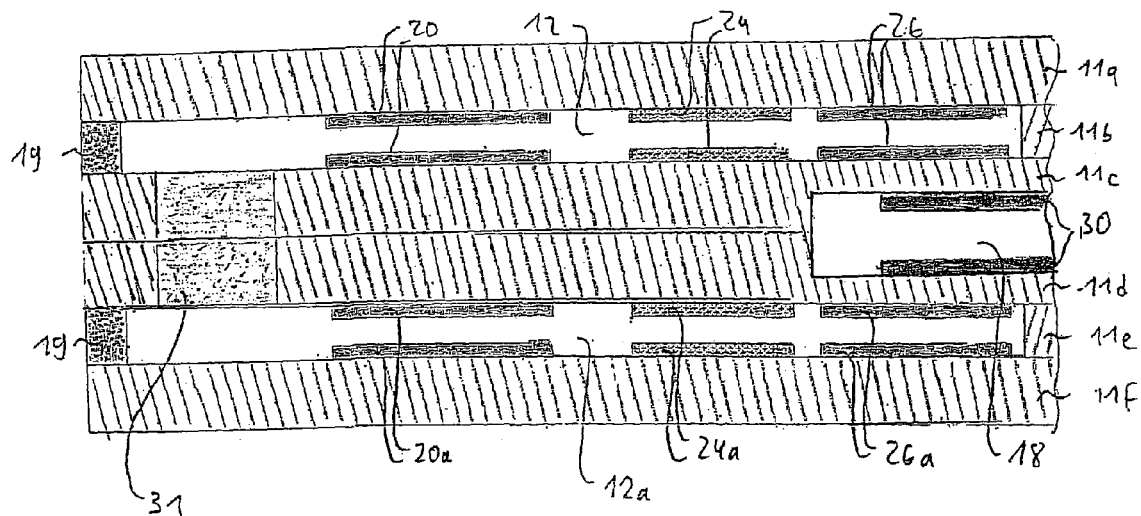
FIG. 5 shows a longitudinal cross section of the measuring-gas-side portion of a sensor element according to the present invention, in the vertical direction, according to a fourth exemplary embodiment.

FIG. 5 depicts a fourth exemplary embodiment of the present invention. In this context, identical reference numerals continue to designate the same components. The sensor element shown in FIG. 5 represents a modification of the sensor element shown in FIG. 4. It additionally has at least one bore in solid-electrolyte layers 11c, 11d, which is filled in with a porous diffusion barrier 31 and interconnects measuring-gas compartments 12, 12a. The cross-section (cross-sectional area) of diffusion barrier 31 may be larger (greater) than the inner diameter (inside width) of measuring-gas compartments 12, 12a. In this manner, it is ensured in a particularly effective manner, that the gas mixture to be measured experiences the same diffusion resistance prior to reaching measuring-gas compartments 12, 12a.

A further specific embodiment of the sensor element shown in FIG. 5 provides for first auxiliary electrodes 20 in measuring-gas compartment 12 to be made of a material different from that of further, first auxiliary electrodes 20a in second measuring-gas compartment 12a. In this context, first auxiliary electrodes 20 are made of a material on which ammonia is not oxidized, when a potential of −200 to −400 mV provided for the removal of oxygen and/or nitrogen oxides is applied. Examples of such a material include a basic oxide, such as $K_2O$ or $Li_2O$, or an oxide of the rare-earth metals. Even precious metals impregnated with basic oxides are suitable.

A material, which catalyzes the oxidation of ammonia when a potential of −200 to −400 mV is applied, is provided for further, first auxiliary electrodes 20a. For example, platinum or a platinum-gold alloy is selected as a material. The advantage of this specific embodiment is that the same potential may be applied to all first auxiliary electrodes 20, 20a and that, consequently, first auxiliary electrodes 20, 20a may be electrically interconnected and only a lead is required.

If the material of further, second auxiliary electrodes 24a is selected so that complete oxidation of ammonia occurs at the provided potential of −200 to −400 mV, then second auxiliary electrodes 24, 24a may be electrically connected to first auxiliary electrodes 20, 20a and only require a lead. For example, platinum or a platinum-gold alloy is suitable as a material.

The material of second auxiliary electrodes 24 in measuring-gas compartment 12 may be selected so that the reduction of nitrogen monoxide at the provided potential of −200 to −400 mV is suppressed as much as possible. For example, platinum or a platinum-gold alloy is provided as a material.

Since nitrogen oxides are reduced at measuring electrodes 26, 26a in both measuring-gas compartment 12 and measuring-gas compartment 12a, measuring-electrodes 26, 26a may be made of the same material, e.g. platinum, and acted upon by the same potential. Therefore, measuring electrodes 26, 26a may also be electrically contacted to each other and have only a lead.

If the ammonia concentration of the gas mixture in measuring-gas compartment 12 is designed to be such that only oxygen and/or nitrogen oxides are removed at first and second auxiliary electrodes 20, 24, but the ammonia concentration remains unchanged, and ammonia is only oxidized at measuring electrode 26, then measuring electrode 26 is made of a material that catalyzes the oxidation of ammonia. In this case, measuring electrodes 26, 26a are made of different materials.

What is claimed is:

1. A sensor element of a gas sensor for determining a concentration of ammonia in a gas mixture, comprising:
at least one first auxiliary electrode situated in a first measuring gas compartment;
at least one measuring electrode situated in the first measuring gas compartment, a signal generated by the at least one measuring electrode being used at least intermittently to determine the concentration of ammonia;
at least one further first auxiliary electrode situated in a second measuring gas compartment; and
at least one further measuring electrode situated in the second measuring gas compartment, a signal generated by the at least one further measuring electrode being used at least intermittently to determine the sum of the concentration of ammonia and nitrogen oxides;
wherein:
the electrodes are positioned downstream in the flow direction of the gas mixture, which are in direct contact with the gas mixture, and
a potential, at which the ammonia contained in the gas mixture is oxidized, is applied at least intermittently to one of the first auxiliary electrode and the at least one measuring electrode and one of the further first auxiliary electrode and the at least one further measuring electrode.

2. The sensor element of claim 1, wherein a potential, at which at least one of oxygen and nitrogen oxides are reduced, is applied to the first auxiliary electrode, a potential, at which the ammonia is oxidized, is applied to the at least one measuring electrode, a potential, at which oxygen is reduced, at which nitrogen oxides are not reduced, is applied to the further first auxiliary electrode, and a potential, at which the ammonia is oxidized, is applied to the at least one further measuring electrode.

3. The sensor element of claim 1, wherein a potential, at which the ammonia contained in the gas mixture is oxidized, is applied to the first auxiliary electrode, a potential, at which an oxidation product of the ammonia is reduced, is applied at least intermittently to the at least one measuring electrode, a potential, at which oxygen is reduced, at which nitrogen oxides are not reduced, and at which the ammonia is oxidized, is applied to the further first auxiliary electrode, and a potential, at which nitrogen oxides are reduced, is applied to the at least one further measuring electrode.

4. The sensor element of claim 3, wherein the oxidation product of the ammonia includes nitrogen monoxide.

5. The sensor element of claim 1, further comprising:
a second auxiliary electrode, which follows the first auxiliary electrode and precedes the at least one measuring electrode in the direction of flow, and
a further second auxiliary electrode, which follows the further first auxiliary electrode and precedes the at least one further measuring electrode in the direction of flow; wherein
a potential is applied to the first auxiliary electrode at which at least one of oxygen and nitrogen oxides are reduced;
a potential is applied to the second auxiliary electrode at which oxygen is reduced and the ammonia is oxidized;
a potential is applied to the further first auxiliary electrode at which oxygen is reduced and nitrogen oxides are not reduced; and
a potential is applied to the further second auxiliary electrode at which oxygen is reduced and the ammonia is oxidized.

6. The sensor element of claim 5, wherein:
the at least one measuring electrode includes two measuring electrodes, which are each preceded by the first auxiliary electrode and the second auxiliary electrode in the flow direction of the gas mixture, and
a potential, at which nitrogen oxides already contained in the gas mixture are decomposed, is applied to the first auxiliary electrode.

7. The sensor element of claim 6, wherein the same potential is applied to the first and the second auxiliary electrodes, and wherein the first auxiliary electrode is made from a first material that does not oxidize ammonia when the potential is applied and the second auxiliary electrodes is made from a second material that catalyzes the oxidation of ammonia when the potential is applied.

8. The sensor element of claim 1, wherein a common diffusion barrier is placed in front of at least one of the at least one measuring electrode and the at least one further measuring electrode in a diffusion direction of the gas mixture.

9. The sensor element of claim 1, wherein the gas sensor for determining a concentration of ammonia also determines at least one further component of the gas mixture.

10. The sensor element of claim 9, wherein the gas mixture includes an exhaust gas of a combustion engine.

11. An emission control system for an internal combustion engine, comprising:
a sensor element of a gas sensor for determining a concentration of ammonia in a gas mixture of an exhaust gas of the internal combustion engine, including:
at least one first auxiliary electrode situated in a first measuring gas compartment;
at least one measuring electrode situated in the first measuring gas compartment, a signal generated by the at least one measuring electrode being used at least intermittently to determine the concentration of ammonia;
at least one further first auxiliary electrode situated in a second measuring gas compartment; and
at least one further measuring electrode situated in the second measuring gas compartment, a signal generated by the at least one further measuring electrode being used at least intermittently to determine the sum of the concentration of ammonia and nitrogen oxides;
wherein:
the electrodes are positioned downstream in the flow direction of the gas mixture, which are in direct contact with the gas mixture, and
a potential, at which the ammonia contained in the gas mixture is oxidized, is applied at least intermittently to one of the first auxiliary electrode and the at least one measuring electrode and one of the further first auxiliary electrode and the at least one further measuring electrode.

12. An emission control system for an internal combustion engine, comprising:
a sensor element of a gas sensor for determining a concentration of an ammonia-oxidation product of a gas mixture of an exhaust gas of the internal combustion engine, by performing the following:
inside the sensor element, at least intermittently oxidizing ammonia present in the gas mixture in a first step; and
determining the concentration of the ammonia-oxidation product at least intermittently in a second step;
the sensor element of the gas sensor, including:
at least one first auxiliary electrode situated in a first measuring gas compartment;
at least one second auxiliary electrode situated in the first measuring gas compartment;
at least one measuring electrode situated in the first measuring gas compartment, a signal generated by the measuring electrode being used at least intermittently to determine the concentration of the ammonia-oxidation product of the gas mixture of the exhaust gas of the internal combustion engine;
at least one further first auxiliary electrode situated in a second measuring gas compartment;
at least one further second auxiliary electrode situated in a second measuring gas compartment; and
at least one further measuring electrode situated in the second measuring gas compartment, a signal generated by the further measuring electrode being used to at least intermittently determine the sum of the concentration of the ammonia-oxidation product and a concentration of nitrogen oxides already present in the gas mixture from the start;
wherein:
the electrodes are positioned downstream in the flow direction of the gas mixture, which are in direct contact with the gas mixture, and
a potential, at which the ammonia contained in the gas mixture is oxidized, is applied at least intermittently to one of the first auxiliary electrode and the at least one measuring electrode and one of the further first auxiliary electrode and the at least one further measuring electrode.

* * * * *